(12) United States Patent
Kleinguetl et al.

(10) Patent No.: US 11,193,342 B2
(45) Date of Patent: Dec. 7, 2021

(54) METHODS FOR DETERMINING THE WATER CONTENT OF A DRILLING FLUID USING WATER PHASE SALINITY

(71) Applicant: Halliburton Energy Services, Inc., Houston, TX (US)

(72) Inventors: Kevin Gregory Kleinguetl, Kingwood, TX (US); Drew A. Fowler, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 135 days.

(21) Appl. No.: 16/846,884

(22) Filed: Apr. 13, 2020

(65) Prior Publication Data

US 2020/0240221 A1    Jul. 30, 2020

Related U.S. Application Data

(62) Division of application No. 15/551,688, filed as application No. PCT/US2016/051690 on Sep. 14, 2016, now abandoned.

(51) Int. Cl.
| | |
|---|---|
| *E21B 21/06* | (2006.01) |
| *E21B 21/08* | (2006.01) |
| *G01N 33/28* | (2006.01) |
| *G01N 33/18* | (2006.01) |

(52) U.S. Cl.
CPC ............ *E21B 21/062* (2013.01); *E21B 21/08* (2013.01); *G01N 33/18* (2013.01); *G01N 33/2823* (2013.01); *E21B 21/065* (2013.01)

(58) Field of Classification Search
CPC .......... G01N 33/2823; G01N 33/2847; G01N 33/18; G01N 33/1886; E21B 21/06–068; E21B 21/08; E21B 49/08
USPC ..................................................... 73/152.04
See application file for complete search history.

(56) References Cited

U.S. PATENT DOCUMENTS

| | | | |
|---|---|---|---|
| 2,513,388 A | 7/1950 | Milton | |
| 3,524,346 A | 8/1970 | Schmidt | |
| 5,103,181 A | 4/1992 | Gaisford et al. | |
| 5,140,527 A | 8/1992 | Jones et al. | |

(Continued)

OTHER PUBLICATIONS

International Search Report and Written Opinion for International Application No. PCT/US2016/051690 dated May 10, 2017 (12 pages).

(Continued)

*Primary Examiner* — David L Singer
(74) *Attorney, Agent, or Firm* — Haynes and Boone, LLP

(57) ABSTRACT

Methods for monitoring a drilling process that uses a drilling fluid are described. The methods include measuring an initial salinity of a water phase of the drilling fluid, diluting the drilling fluid with a known amount of water to form a diluted drilling fluid, measuring a salinity of a water phase of the diluted drilling fluid, determining an initial relationship between a salt content and a water content in the drilling fluid using the initial salinity of the water phase of the drilling fluid, calculating an initial water content of the drilling fluid using the measured salinity of the diluted drilling fluid and the initial relationship between the salt content and the water content in the drilling fluid, and adjusting one or more drilling parameters in response to the calculated initial water content.

10 Claims, 4 Drawing Sheets

(56) References Cited

U.S. PATENT DOCUMENTS

| | | | |
|---|---|---|---|
| 5,239,862 | A | 8/1993 | Atkinson |
| 5,519,214 | A | 5/1996 | Houwen et al. |
| 5,854,820 | A | 12/1998 | Slijkerman et al. |
| 8,058,885 | B2 | 11/2011 | Caron |
| 2007/0287190 | A1 | 12/2007 | Chevalier et al. |
| 2010/0204511 | A1 | 8/2010 | Horton |
| 2011/0000713 | A1 | 1/2011 | Meeten et al. |
| 2012/0094876 | A1 | 4/2012 | Jamison et al. |
| 2013/0085675 | A1 | 4/2013 | Prakash et al. |
| 2013/0158875 | A1 | 6/2013 | Brown |
| 2014/0333307 | A1 | 11/2014 | Ahmad et al. |
| 2015/0211350 | A1 | 7/2015 | Norman |
| 2015/0268374 | A1 | 9/2015 | Rapoport |
| 2016/0202231 | A1* | 7/2016 | Black .................. G01N 27/221 73/61.46 |
| 2017/0321504 | A1 | 11/2017 | Ye et al. |

OTHER PUBLICATIONS

National Institutes of Health, Office of Intramural Training & Education's Webinar on Laboratory Math II: Solutions and Dilutions (Year: 2013).

Merz et al., Measuring Mountain Stream Discharge Using the Salt Dilution Method (Year: 2006).

Forstonlabs, Conductivity Probe (Order Code NavCT) (Year: 2010).

O'Haver, Comparison of analytical calibration methods (Year: 2014).

\* cited by examiner

METHODS FOR DETERMINING THE WATER CONTENT OF A DRILLING FLUID USING WATER PHASE SALINITY

CROSS-REFERENCE TO RELATED APPLICATIONS

The present application is a divisional of U.S. patent application Ser. No. 15/551,688, filed Aug. 17, 2017, which is a U.S. National Stage patent application of International Patent Application No. PCT/US2016/051690, filed on Sep. 14, 2016, the benefit of which is claimed and the disclosure of which is incorporated herein by reference in its entirety.

BACKGROUND

The present invention relates generally to monitoring a drilling process that uses a drilling fluid, such as an oil-based mud (OBM), synthetic-based mud (SBM), or water-based mud (WBM). In particular, the present invention relates to methods of determining the total initial water content of a drilling fluid using the salinity of the water phase of the drilling fluid.

A drilling fluid or mud is a specifically designed fluid that is circulated through a wellbore from the surface down to the bottom of the hole being drilled. The drilling fluid transports the cuttings from the drill bit, cooling and lubricating the drill bit, and provides pressure to the walls of the wellbore, which helps maintain its integrity, thus preventing well blowouts. Thus, it is important to continuously monitor the characteristics of the drilling fluid. More particularly, it is important to monitor the water content of the drilling fluid to determine if the drilling fluid is gaining water or losing water to the formation, and to keep the salinity of the drilling fluid the same throughout the drilling process. When coupled with other measurements, the water content for an OBM or SBM can provide the average specific gravity of the solids (ASG) and the oil/water ratio (OWR). For a WBM, the water content along with the density of the fluid can directly give provide the amount of low gravity solids (LGS) in the system.

Invert-emulsion drilling fluids are typically used because of their superior rheological profile as well as for increasing the rate of penetration and wellbore stability. For example, invert-emulsion drilling fluids are stable over a wide range of conditions due to their low viscosity and yield strengths and higher temperatures. This rheological profile allows for reduced salt content, maximum penetration rate, better solids separation, and reduced surface losses.

Invert-emulsion drilling fluids are oil-based drilling fluids that generally consist of a continuous phase of oil, a discontinuous phase of brine, and solids in suspension. The combination of the continuous oil phase, discontinuous brine phase, and the suspended solids give the drilling fluid the properties that aid in the drilling of a well. The brine in the invert-emulsion drilling fluid contributes to achieving the desired rheology properties in the drilling fluid so as to reduce the overall cost in drilling. Knowledge of the salinity of the brine is especially important to prevent the water in the mud from moving into the surrounding formation, which would result in wet and mushy cuttings.

Analyses of drilling fluid characteristics have been previously accomplished. However, such measurements normally require the collection of process samples and subsequent laboratory testing. A typical "retort" analysis allows for the determination of the relative amounts of water, oil, and solids by simple laboratory distillation. However, this process takes a great amount of time and the high temperatures limit the rate of repeatability. Conventionally, process mud samples are collected every 6-24 hours. Even if samples are collected and analyzed more frequently, there is still a substantial gap in time between when the drilling fluid characteristics are present in the drilling operation, (i.e., when the sample is obtained), and when the laboratory testing results are available. Thus, the use of a retort method is both time and labor intensive.

To optimize the performance of a drilling fluid during drilling operations, the physical and chemical properties of the drilling fluid and its component parts must be carefully monitored and controlled. As such, there is a continued and ongoing need for improved methods of determining the water content of the drilling fluid.

BRIEF DESCRIPTION OF THE DRAWINGS

The following figures are included to illustrate certain aspects of the present invention, and should not be viewed as an exclusive embodiment. The subject matter disclosed is capable of considerable modification, alteration, and equivalents in form and function, as will occur to those of ordinary skill in the art and having the benefit of this disclosure.

DETAILED DESCRIPTION

Figure 1:
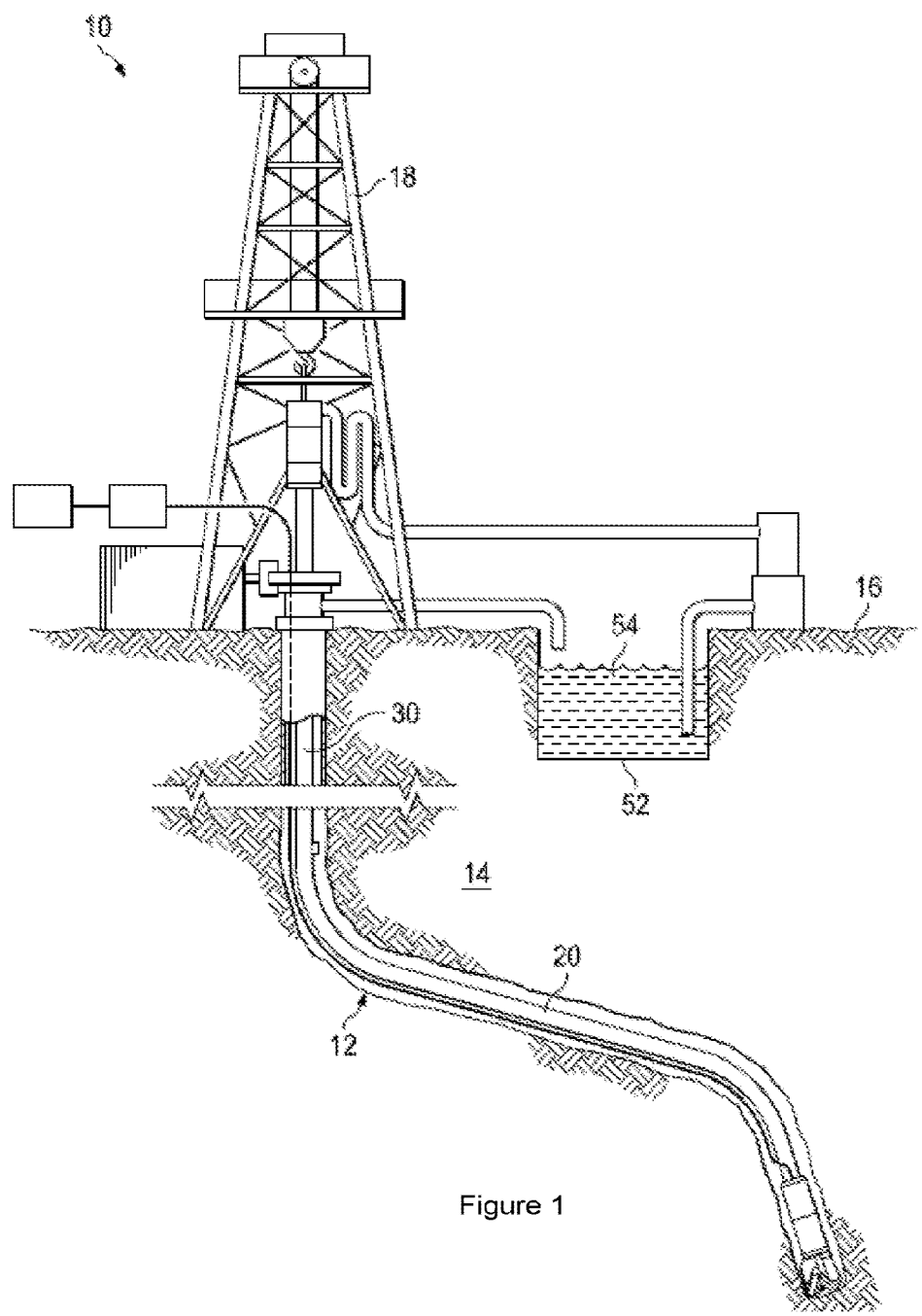
FIG. 1 illustrates a land-based drilling and production system.

The present invention provides methods for monitoring the characteristics of a drilling fluid (e.g., an oil-based drilling fluid or a water-based drilling fluid) used during the drilling process. An oil-based drilling fluid generally includes an external phase of an invert emulsion, an internal phase of a saline, aqueous solution, emulsifiers, and other agents or additives for suspension, weight, density, oil-wetting, and rheology control. As used herein, "oil-based drilling fluid" means a drilling fluid that is an emulsion containing oil as the continuous phase and brine as the dispersed or discontinuous phase. According to several exemplary embodiments, the oil may be one or more synthetic oils, as well as natural or traditional oils. A water-based drilling fluid generally includes an external phase of water and additives for suspension, weight, density, oil-wetting, salinity and rheology control. The water-based drilling might also have a discontinuous phase of oil.

According to several exemplary embodiments, the methods involve measuring the initial salinity of the water phase of the drilling fluid, diluting the drilling fluid with water, and re-measuring the salinity. More dilutions can be performed to increase the accuracy of the measurements. Knowing the water added and the salinities of the water phases, the original or initial water content of the drilling fluid can be back calculated. Advantageously, these methods are faster and more efficient compared to current drilling fluid monitoring methods.

According to several exemplary embodiments, a method of monitoring a drilling process that uses a drilling fluid is described. The method includes measuring an initial salinity of a water phase of the drilling fluid, diluting the drilling fluid with a known amount of water having a known salinity to form a diluted drilling fluid, measuring the salinity of a water phase of the diluted drilling fluid, determining an initial relationship between a salt content and a water content in the drilling fluid using the initial salinity of the water phase of the drilling fluid, calculating an initial water content of the drilling fluid using the measured salinity of the diluted drilling fluid and the initial relationship between the salt content and the water content in the drilling fluid, and adjusting one or more drilling parameters in response to the calculated initial water content. According to several exemplary embodiments, the method is performed in real-time or near real-time.

According to several exemplary embodiments, the one or more drilling parameters includes, but is not limited to, the composition of the drilling fluid, a solids removal treatment, rate of penetration (ROP), flow rate of the drilling fluid, or any combination thereof. According to several exemplary embodiments, the method further includes communicating the calculated initial water content to a drill crew. According to several exemplary embodiments, the initial water salinity or the salinity of the diluted drilling fluid is measured using a salinity meter, and the measurement is performed in real-time.

According to several exemplary embodiments, the initial salinity of the drilling fluid and the salinity of the diluted drilling fluid is measured in any suitable way. Suitable methods include, but are not limited to, titrating the water phase of the drilling fluid and the water phase of the diluted drilling fluid, measuring an electrochemical impedance of the water phase of the drilling fluid and the water phase of the diluted drilling fluid, measuring an electrical conductivity of the water phase of the drilling fluid and the water phase of the diluted drilling fluid, measuring a dielectric constant of the water phase of the drilling fluid and the water phase of the diluted drilling fluid, and measuring a thermal conductivity of the water phase of the drilling fluid and the water phase of the diluted drilling fluid.

According to several exemplary embodiments, the method further includes diluting the drilling fluid with a second, different known amount of water to form a second diluted drilling fluid, and measuring a salinity of a water phase of the second diluted drilling fluid. According to several exemplary embodiments, the method further includes calculating an initial water content of the drilling fluid using the measured salinity of the second diluted drilling fluid and the initial relationship between the salt content and the water content in the drilling fluid.

According to several exemplary embodiments, the method further includes determining an oil/water ratio of an oil-based drilling fluid or an average specific gravity or percent solids content of an oil-based drilling fluid or water-based drilling fluid, when coupled with other measurements such as the density of the drilling fluid. According to several exemplary embodiments, the oil/water ratio, or the average specific gravity of the solids, or both are determined in real-time.

According to several exemplary embodiments, another method of monitoring a drilling process that uses a drilling fluid is provided. The method includes measuring an initial salinity of a water phase of the drilling fluid, diluting the drilling fluid with a known amount of water having a known salinity to form a diluted drilling fluid, measuring a salinity of a water phase of the diluted drilling fluid, determining an initial relationship between a salt content and a water content in the drilling fluid using the initial salinity of the water phase of the drilling fluid, calculating an initial water content of the drilling fluid using the measured salinity of the diluted drilling fluid and the initial relationship between the salt content and the water content in the drilling fluid, continuously monitoring the water content of the drilling fluid, and adjusting one or more drilling parameters in response to the calculated initial water content and the continuously monitored water content. According to several exemplary embodiments, the method is performed in real-time.

According to several exemplary embodiments, the one or more drilling parameters includes, but is not limited to, the composition of the drilling fluid, a solids removal treatment, rate of penetration (ROP), flow rate of the drilling fluid, or any combination thereof. According to several exemplary embodiments, the method further includes communicating the calculated initial water content to a drill crew.

According to several exemplary embodiments, the method further includes diluting the drilling fluid with a second, different known amount of water having a known salinity to form a second diluted drilling fluid, and measuring a salinity of a water phase of the second diluted drilling fluid. According to several exemplary embodiments, the method further includes calculating a water content of the drilling fluid using the measured salinity of the second diluted drilling fluid and the initial relationship between the salt content and the water content in the drilling fluid.

According to several exemplary embodiments, the method further includes determining an oil/water ratio of the oil-based drilling fluid, or an average specific gravity of the solids or percent solids content of the oil-based drilling fluid or water-based drilling fluid, when coupled with other measurements such as the density of the drilling fluid. According to several exemplary embodiments, the oil/water ratio, or the average specific gravity of the solids, or both are determined in real-time.

According to several exemplary embodiments, yet another method of monitoring a drilling process that uses a drilling fluid is provided. The method includes diluting the drilling fluid with a known amount of water to form a diluted drilling fluid, measuring a salinity of a water phase of the diluted drilling fluid, providing an equation for an initial salt content in the diluted drilling fluid, wherein the equation includes:

$$S_{a1}(W_i+W_{a1}+W_s)=W_s \qquad \text{(equation 1)}$$

where:
$W_i$=initial water content (in grams),
$W_s$=initial salt content (in grams),
$W_{a1}$ known amount of water used in dilution to form the diluted drilling fluid (in grams), and
$S_{a1}$=measured salinity of the water phase of the diluted drilling fluid (as a decimal), diluting the drilling fluid with a second, different known amount of water to form a second diluted drilling fluid, measuring a salinity of a water phase of the second diluted drilling fluid, providing an equation for an initial salt content in the second diluted drilling fluid, wherein the equation includes:

$$S_{a2}(W_i+W_{a2}+W_s)=W_s \qquad \text{(equation 2)}$$

where:
$W_i$=initial water content (in grams),
$W_s$=initial salt content (in grams),
$W_{a2}$=known amount of water used in dilution to form the second diluted drilling fluid (in grams), and $S_{a2}$=measured salinity of the water phase of the second diluted drilling fluid (as a decimal);
calculating the initial water content of the drilling fluid using equations 1 and 2, and adjusting one or more drilling parameters in response to the calculated initial water content of the drilling fluid. According to several exemplary embodiments, the initial water phase salinity is not required to determine the initial water content.

According to several exemplary embodiments, the method further includes diluting the drilling fluid with a third known amount of water to form a third diluted drilling fluid, measuring a salinity of a water phase of the third diluted drilling fluid, providing an equation for an initial salt content in the third diluted drilling fluid, wherein the equation includes:

$$S_{a3}(W_i+W_{a3}+W_s)=W_s \qquad \text{(equation 3)}$$

where:
$W_i$=initial water content (in grams),
$W_s$=initial salt content (in grams),
$W_{a3}$=known amount of water used in dilution to form the diluted drilling fluid (in grams), and
$S_{a3}$=measured salinity of the water phase of the diluted drilling fluid (as a decimal), and calculating the initial water content of the drilling fluid using equations 1 and 3 or equations 2 and 3.

According to several exemplary embodiments, the method is performed in real-time. According to several exemplary embodiments, the one or more drilling parameters include, but is not limited to, the composition of the drilling fluid, a solids removal treatment, rate of penetration (ROP), flow rate of the drilling fluid, or any combination thereof.

According to several exemplary embodiments, the method further includes determining an oil/water ratio of an oil-based drilling fluid, or an average specific gravity of the solids or percent solids content of an oil-based drilling fluid or water-based drilling fluid, in real-time. According to several exemplary embodiments, the method further includes communicating at least one of the calculated initial water contents to a drill crew.

Turning to FIG. 1, shown is an elevation view in partial cross-section of a wellbore drilling and production system 10 utilized to produce hydrocarbons from wellbore 12 extending through various earth strata in an oil and gas formation 14 located below the earth's surface 16. Drilling and production system 10 may include a drilling rig or derrick 18 to perform various activities related to drilling or production, such as the methods described below. Likewise, drilling and production system 10 may include various types of tools or equipment 20 supported by rig 18 and disposed in wellbore 12 for performing these activities.

A working or service fluid source 52, such as a storage tank or vessel, may supply a working fluid 54 that is pumped to the upper end of tubing string 30 and flows through tubing string 30. Working fluid source 52 may supply any fluid utilized in wellbore operations, including without limitation, drilling fluid or mud (e.g., an oil-based drilling fluid), slurry, acidizing fluid, liquid water, steam, hydraulic fracturing fluid, propane, nitrogen, carbon dioxide or some other type of fluid.

According to several exemplary embodiments, the methods of the present invention measure the water phase salinity of the drilling fluid to determine the original water content of the drilling fluid. The water phase salinity may be measured using any method known to those of ordinary skill in the art, including, but not limited to, the use of refractometers, hydrometers, conductive meters, salinity meters, and titration equipment. According to several exemplary embodiments, the water phase salinity is measured in real-time using a salinity meter. According to several exemplary embodiments, the salinity of water can be obtained by measuring the electrical conductivity of the water, the thermal conductivity of the water, the electrical impedance of the water, and/or the dielectric constant of the water.

According to several exemplary embodiments, determinations may be made using the obtained water phase salinity, including calculations to determine the original or initial water content of the drilling fluid. This initial water content can then be used to optimize drilling fluid properties or qualities, and/or drilling operation performance, conditions, situations, or events.

For example, the initial water content can be used in combination with current water content (or current water phase salinity) to determine if there is undesirable water flow into the wellbore from the formation. An influx of water, without there being an adequate concentration of emulsifier, wetting agent, and other components added to accommodate the water influx, can lead to a phenomenon known in the art as "clobbered up" or "gelled up" mud, whereby the active mud system can become undesirably highly viscous. Water influx issues can also result in fluctuations in equivalent circulating density (ECD)/equivalent static density (ESD), and circulating pressure, as well as reduced pump rate, and can induce formation losses, which result in surge/swab issues, and significantly increase the cost and time of treatment. Once it is determined that a water influx is occurring, actions can be taken to immediately treat the contaminated mud using an adequate amount of specific product(s). For example, emulsifier, wetting agent, weighting agent, lost circulation materials and/or lime may be added to quickly adjust the mud properties, thereby preventing re-circulating the "clobbered up" mud back down the wellbore where it can potentially result in NPT (non-productive time) and/or a shutdown.

In another example, drilling operations can result in a loss of water into the formation. Such migration of water into the formation occurs when drilling mud penetrates the formation and properties of the formation result in retention of water therein. In typical drilling operations, a filter cake (a composite of various solids suspended in the active mud), is deposited within the porous media of the formation when mud enters the formation. This deposition of filter cake is used to control the amount of filtrate being lost to the formation at all times, and thus excess water retention in the formation can be due to inadequate filter cake quality. This formation fluid loss can be controlled using specific drilling fluid products that form the filter cake. One detrimental effect of excessive amounts of water lost to the formation is the potential for an inadequate bond between the casing and the wellbore wall during cementing operations. Continuous monitoring of water losses from the active mud into the formation provides information that can be used to make determinations regarding the viability and/or requisite methodology of future cementing operations.

According to several exemplary embodiments, if the continuously obtained water content data is indicative of unacceptable water loss into the formation (e.g., exceeds a specified amount), this information can be communicated, either directly or indirectly, to the drill crew so that fluid treatment options can be timely initiated to avoid the possibility of having to perform costly cement job remediation procedures. According to several exemplary embodiments, a computerized instrument, such as a programmable logic controller (PLC), can be utilized to automatically adjust the drilling operations as would be desired in such a water loss situation based on the continuously obtained water content data being communicated, either directly or indirectly.

Water and salt content in the drilling fluid affect drilling operations in additional ways. For instance, the combination of a high salinity formation and low salinity drilling fluid can result in an osmotic flow of water from drilling fluid into the formation causing the formation to hydrate, resulting in a swelling wellbore, which can result in a stuck pipe incident. The reverse situation, a low salinity formation and a high salinity drilling fluid, resulting in osmotic water flow from the formation into the drilling fluid, can produce a brittle, unstable wellbore that could potentially collapse, which can also result in a stuck pipe incident. Accordingly, it is advantageous that the water content of the drilling fluid and salinity measurements be calibrated against wellbore flow conditions to assure that there is an osmotic balance between the fluid entering the well in relation to the fluid exiting the well.

According to several exemplary embodiments, the oil and water information, including oil/water ratio in the active mud and average specific gravity of the solids, is obtained continuously and can be utilized to control drilling operations. For example, it is generally known in the art that the oil/water ratio affects the "emulsion stability," which is a measure of how well the water is being emulsified into the oil of the oil-based drilling fluid. Deviations from an optimal oil/water ratio in the oil-based drilling fluid can lead to an increase in water wet solids. That is, hydrated solids in the oil-based drilling system adhering to each other and aggregating such that they tend to settle or sag, and adhere to metal surfaces. Such an increase in water wet solids is typically due to too low an oil/water ratio (i.e., too much water and/or too little oil) without adequate emulsifier and wetting agent, and tends to destabilize the emulsion. An influx of water can cause such an emulsion stability decrease, that can result in shaker screen blinding, and/or an increase in equivalent circulating density (ECD) that can result in sloughing (i.e., the partial or complete collapse of the wellbore resulting from incompetent, unconsolidated formations and wetting along the bedding planes). According to several exemplary embodiments, if the oil/water ratio data is indicative of conditions giving rise to an emulsion instability, this information can be communicated, either directly or indirectly, to the drill crew so that the oil/water ratio in the drilling fluid can be appropriately adjusted. The addition of water can also increase the viscosity of the drilling fluid and this increased viscosity can be dealt in different ways than if the viscosity was increased by other methods (i.e., viscosifier or an increase in solids).

According to several exemplary embodiments, various characteristics of the drilling fluid are measured via inline instruments, where the measurement information is obtained as real-time data or near real-time data. According to several exemplary embodiments, the in-line measurement information, as well as other information and data, are communicated to and/or stored within a processing device, including but not limited to, a computerized instrument, such as a PLC, which is adapted to communicate information and data, directly or indirectly, to a drill crew, and/or utilize the information and data, directly or indirectly, to control one or more devices during a drilling operation.

According to several exemplary embodiments, the initial water content of the drilling fluid is communicated to a drill crew. This communication may be in the form of an electronic notification, alert, or alarm (e.g., via computer), and/or a non-computerized notification, alert, or alarm, including but not limited to, visual, audial, and mechanical events.

According to several exemplary embodiments, the water content of the drilling fluid is continuously measured. The water content can be obtained via an inline instrument utilizing ultrasonic, magnetic resonance imaging (MM), dielectric constant, capacitance, conductivity, resistivity, microwave, resonance-enhanced multivariate impedance spectroscopy (REMIS) technology, or any other suitable in-line real-time method.

Figure 2:
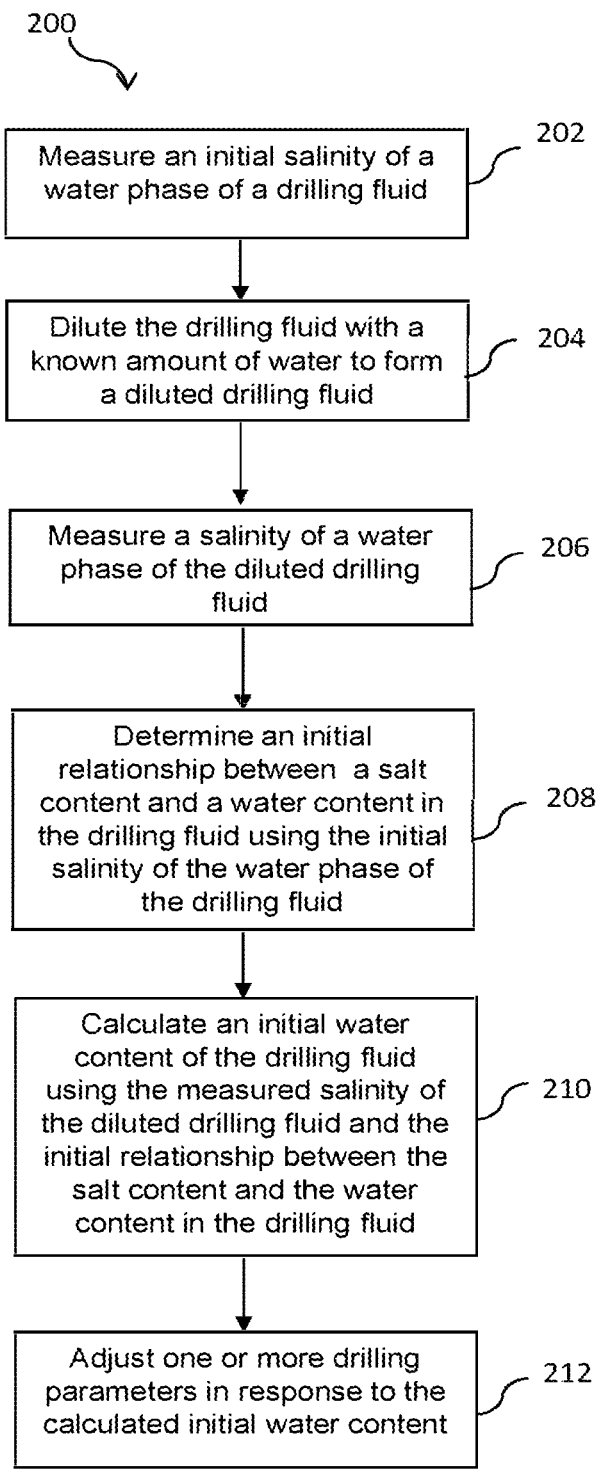
FIG. 2 depicts a method of monitoring a drilling process that uses a drilling fluid according to embodiments of the present invention.

According to several exemplary embodiments, a method of monitoring a drilling process that uses a drilling fluid is provided. Turning now to FIG. 2, method 200 includes measuring an initial salinity of a water phase of the drilling fluid in step 202, diluting the drilling fluid with a known amount of water to form a diluted drilling fluid in step 204, measuring a salinity of a water phase of the diluted drilling fluid in step 206, determining an initial relationship between a salt content and a water content in the drilling fluid using the initial salinity of the water phase of the drilling fluid in step 208, calculating an initial water content of the drilling fluid using the measured salinity of the diluted drilling fluid and the initial relationship between the salt content and the water content in the drilling fluid in step 210, and adjusting one or more drilling parameters in response to the calculated initial water content in step 212.

Figure 3:
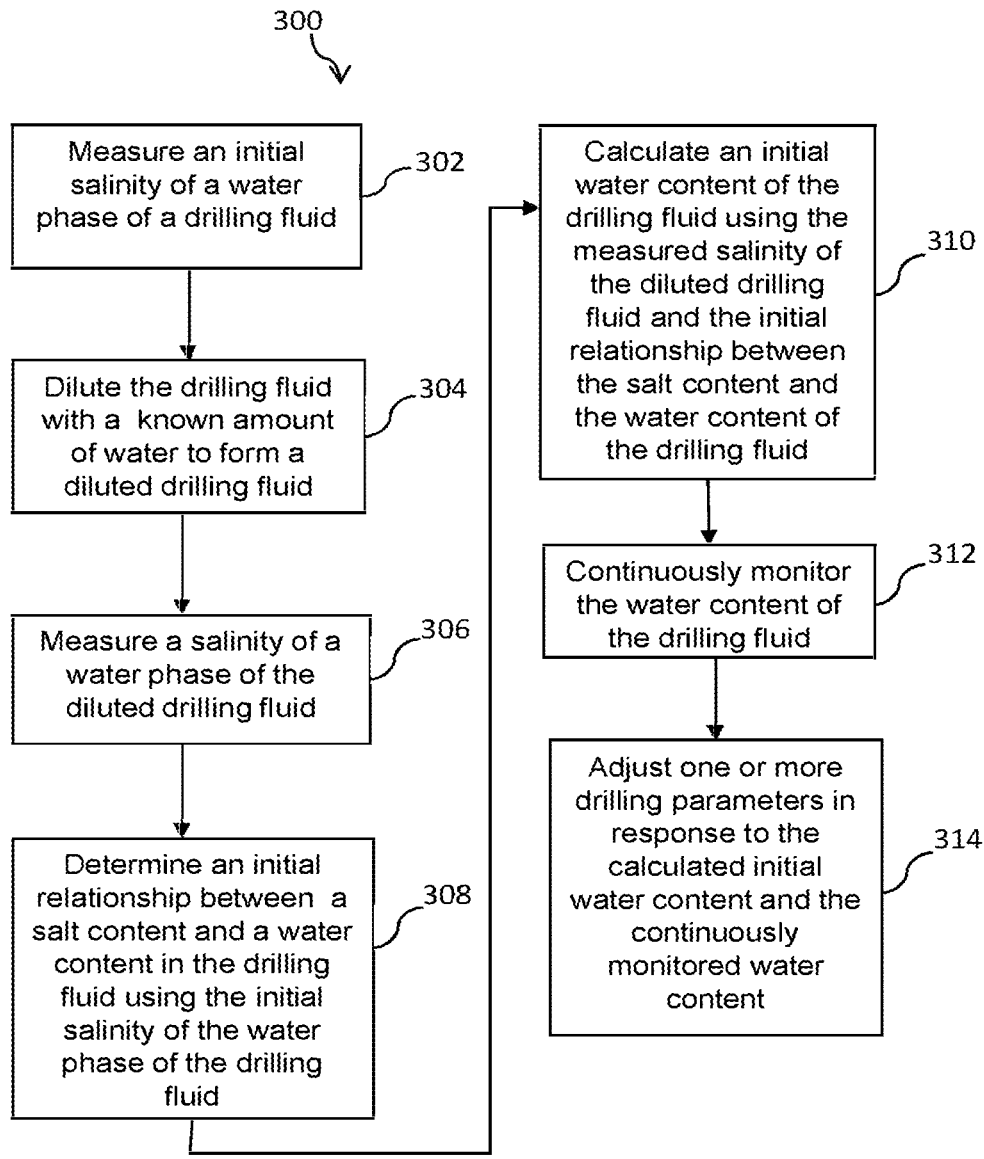
FIG. 3 depicts another method of monitoring a drilling process that uses a drilling fluid according to embodiments of the present invention.

Turning now to FIG. 3, another method 300 of monitoring a drilling process that uses a drilling fluid is provided. The method 300 includes measuring an initial salinity of a water phase of the drilling fluid in step 302, diluting the drilling fluid with a known amount of water to form a diluted drilling fluid in step 304, measuring a salinity of a water phase of the diluted drilling fluid in step 306, determining an initial relationship between a salt content and a water content in the drilling fluid using the initial salinity of the water phase of the drilling fluid in step 308, calculating an initial water content of the drilling fluid using the measured salinity of the diluted drilling fluid and the initial relationship between the salt content and the water content in the drilling fluid in step 310, continuously monitoring the water content of the drilling fluid in step 312, and adjusting one or more drilling parameters in response to the calculated initial water content and the continuously monitored water content in step 314.

Figure 4:
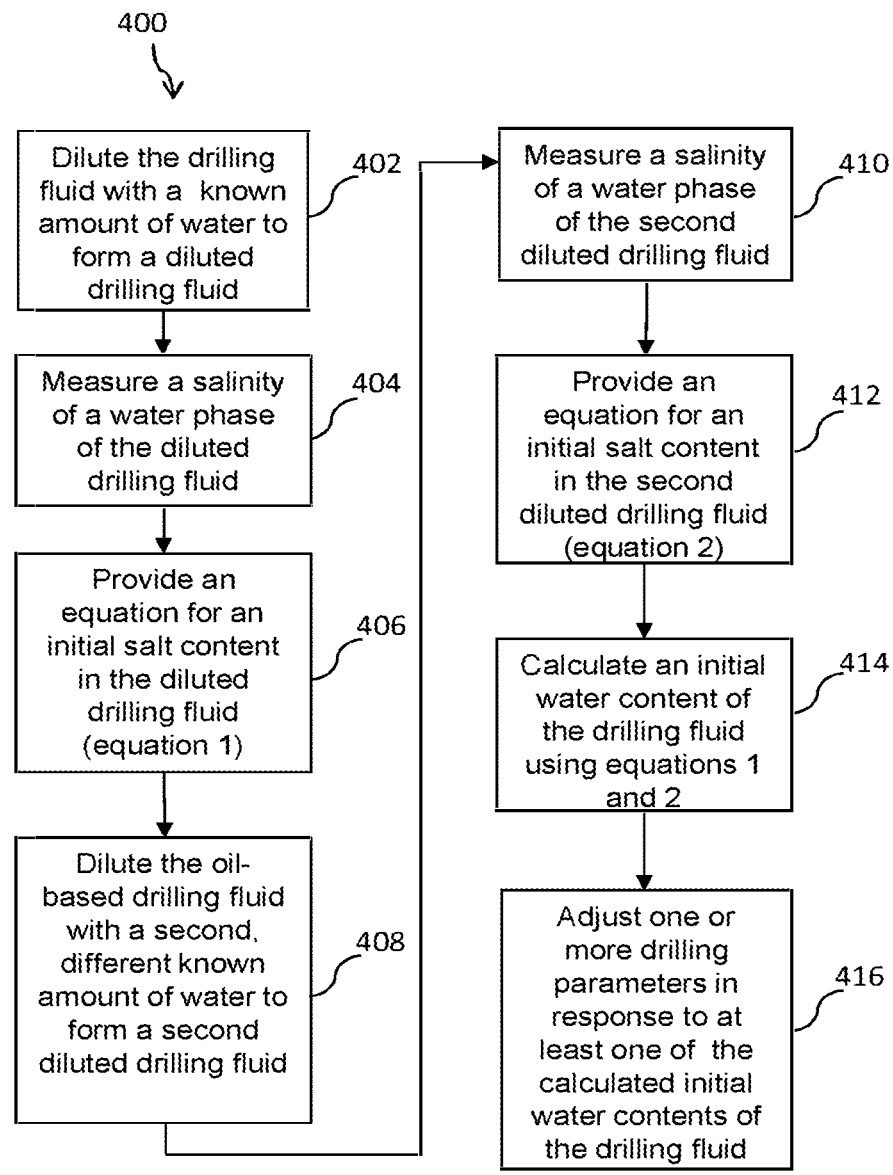
FIG. 4 depicts yet another method of monitoring a drilling process that uses a drilling fluid according to embodiments of the present invention.

FIG. 4 depicts yet another method 400 of monitoring a drilling process that uses a drilling fluid. The method 400 includes diluting the drilling fluid with a known amount of water to form a diluted drilling fluid at step 402, measuring a salinity of a water phase of the diluted drilling fluid at step 404, providing an equation for an initial salt content in the diluted drilling fluid (equation 1) at step 406, diluting the drilling fluid with a second, different known amount of water to form a second diluted drilling fluid at step 408, measuring a salinity of a water phase of the second diluted drilling fluid at step 410, providing an equation for an initial salt content in the second diluted drilling fluid (equation 2) at step 412, calculating an initial water content of the drilling fluid using equations 1 and 2 at step 414, and adjusting one or more drilling parameters in response to the calculated initial water content of the drilling fluid at step 416.

The following exemplary calculations are illustrative of the methods discussed above and are not intended to be limiting.

EXEMPLARY CALCULATIONS

The calculations provided below describe how exemplary embodiments of the present invention would be utilized to determine an initial water content of a water phase of a drilling fluid.

Example 1

An initial water phase salinity of an oil-based drilling fluid was determined to be 25% salinity by mass.

The calculations proceed as follows.

$W_i$ = initial water content (in grams)

$W_s$ = initial salt content (in grams)

$S_i$ = initial salinity measurement (as a decimal)

$$S_i = \frac{W_s}{W_i + W_s}$$

$$0.25 = \frac{W_s}{W_i + W_s}$$

$$W_s = 0.33 W_i$$

The oil-based drilling fluid was diluted 1:1 with 100 g of water, and the resultant water phase salinity is determined to be 7.14% by mass.

$W_a$ = added water (in grams)

$S_a$ = resultant salinity measurement (as a decimal)

$$S_a = \frac{W_s}{W_i + W_a + W_s}$$

$$0.0714 = \frac{W_s}{W_i + 100 \text{ g} + W_s}$$

$$0.0714 = \frac{033 W_i}{W_i + 100 \text{ g} + 0.33 W_i}$$

$$0.0714 = \frac{033 W_i}{100 \text{ g} + 1.33 W_i}$$

$$W_i = 30.38 \text{ grams}$$

The same initial oil-based drilling fluid with 25% salinity by mass was diluted 2:1 with 50 g of water, and the resultant water phase salinity was determined to be 11.11% by mass. Despite the initial oil-based drilling fluid being diluted with twice as much water, the water phase salinity is not halved because of the water initially present in the oil-based drilling fluid.

The calculation proceeds as follows:

$$0.1111 = \frac{W_s}{W_i + 50 \text{ g} + W_s}$$

$$0.1111 = \frac{033 W_i}{W_i + 50 \text{ g} + 0.33 W_i}$$

$$0.1111 = \frac{0.33 W_i}{50 \text{ g} + 1.33 W_i}$$

$$W_i = 30.48 \text{ grams}$$

Example 2

Fifty (50) mL of an oil-based drilling fluid was diluted with different known amounts of water and the resultant water phase salinity measured. The results are provided in Table 1 below.

TABLE 1

| Dilution Ratio | Water Phase Salinity (Percent) | Mud (mL) | Water Added (grams) |
| --- | --- | --- | --- |
| 5:1 | 0.888559709 | 50 | 250 |
| 6:1 | 0.752774146 | 50 | 300 |
| 7:1 | 0.635800629 | 50 | 350 |
| 8:1 | 0.562699141 | 50 | 400 |
| 9:1 | 0.0249918 | 50 | 450 |

The calculations proceed as follows.

$W_i$ = initial water content (in grams)

$W_s$ = initial salt content (in grams)

$W_a$ = added water (in grams)

$S_a$ = resultant salinity measurement (as a decimal)

$$S_a = \frac{W_s}{W_i + W_a + W_s}$$

$$S_a(W_i + W_a + W_s) = W_s$$

Plugging in the numbers from the first example in Table 1 above:

$0.0089(W_i + 250 \text{ g} + W_s) = W_s$ $0.0089 W_i + 2.225 \text{ g} + 0.0089 W_s = W_s$ $0.0089 W_i + 2.225 \text{ g} = 0.99 W_s$ Plugging in the numbers from the third example in Table 1 above:

$0.0064(W_i + 350 \text{ g} + W_s) = W_s$ $0.0064 W_i + 2.24 \text{ g} + 0.0064 W_s = W_s$ $0.0064 W_i + 2.24 \text{ g} = 0.99 W_s$ Since both equations equal $0.99 W_s$:

$0.0089 W_i + 2.225 \text{ g} = 0.0064 W_i + 2.24 \text{ g}$

Solving for $W_i$:

$0.0025 W_i = 0.015 \text{ g}$ $W_i = 6 \text{ g}$

These calculations can be repeated any number of times using the data in Table 1 to get a more accurate initial water content.

Taking the fourth example in Table 1:

$0.0056(W_i + 400 \text{ g} + W_s) = W_s$ $0.0056 W_i + 2.24 \text{ g} + 0.0056 W_s = W_s$ $0.0056 W_i + 2.24 \text{ g} = 0.99 W_s$ Equating the equation of the first example to the equation of the fourth example:

$0.0089 W_i + 2.225 \text{ g} = 0.0056 W_i + 2.24 \text{ g}$

Solving for $W_i$:

$0.0033 W_i = 0.015 \text{ g}$ $W_i = 4.5 \text{ g}$

Taking the fifth example in Table 1

$0.0050(W_i + 450 \text{ g} + W_s) = W_s$ $0.0050 W_i + 2.25 \text{ g} + 0.0050 W_s = W_s$ $0.0050 W_i + 2.25 \text{ g} = 0.99 W_s$ Equating the equation of the first example to the fifth example:

0.0089$W_i$+2.225 g=0.0050$W_i$+2.25 g

Solving for $W_i$:

0.0039$W_i$=0.025 g $W_i$=6.41 g

As can be seen, the initial water contents are slightly different, so additional calculations may be made to determine what other values are obtained. These other values are compared to determine a more accurate value of the initial water content. Although only a few exemplary embodiments have been described in detail above, those of ordinary skill in the art will readily appreciate that many other modifications are possible in the exemplary embodiments without materially departing from the novel teachings and advantages of the present invention. Accordingly, all such modifications are intended to be included within the scope of the present invention as defined in the following claims.

What is claimed is:

1. A method of monitoring a drilling process that uses a drilling fluid comprising:
    diluting the drilling fluid with a known amount of water to form a diluted drilling fluid;
    measuring a salinity of a water phase of the diluted drilling fluid;
    providing an equation for an initial salt content in the diluted drilling fluid, wherein the equation comprises:

$$S_{a1}(W_i+W_{a1}+W_s)=W_s \quad \text{(equation 1)}$$

where:
   $W_i$=initial water content in grams,
   $W_s$=initial salt content in grams,
   $W_{a1}$=known amount of water used in dilution to form the diluted drilling fluid in grams, and
   $S_{a1}$=measured salinity of the water phase of the diluted drilling fluid as a decimal;
    diluting the drilling fluid with a second, different known amount of water to form a second diluted drilling fluid;
    measuring a salinity of a water phase of the second diluted drilling fluid;
    providing an equation for an initial salt content in the second diluted drilling fluid, wherein the equation comprises:

$$S_{a2}(W_i+W_{a2}+W_s)=W_s \quad \text{(equation 2)}$$

where:
   $W_i$=initial water content in grams,
   $W_s$=initial salt content in grams,
   $W_{a2}$=known amount of water used in dilution to form the second diluted drilling fluid in grams, and
   $S_{a2}$=measured salinity of the water phase of the second diluted drilling fluid as a decimal;
    calculating the initial water content of the drilling fluid using equations 1 and 2; and
    adjusting one or more drilling parameters in response to the calculated initial water content of the drilling fluid.

2. The method of claim 1, further comprising:
    diluting the drilling fluid with a third known amount of water to form a third diluted drilling fluid;
    measuring a salinity of a water phase of the third diluted drilling fluid;
    providing an equation for an initial salt content in the third diluted drilling fluid, wherein the equation comprises:

$$S_{a3}(W_i+W_{a3}+W_s)=W_s \quad \text{(equation 3)}$$

where:
   $W_i$=initial water content in grams,
   $W_s$=initial salt content in grams,
   $W_{a3}$=known amount of water used in dilution to form the diluted drilling fluid in grams, and
   $S_{a3}$=measured salinity of the water phase of the diluted drilling fluid as a decimal); and
    calculating the initial water content of the drilling fluid using equations 1 and 3 or equations 2 and 3.

3. The method of claim 1, further comprising determining an oil/water ratio of the drilling fluid, or an average specific gravity of solids for the drilling fluid, or both.

4. The method of claim 3, wherein the oil/water ratio, or the average specific gravity, or both are determined in real-time.

5. The method of claim 1, wherein measuring the salinity of the water phase of the diluted drilling fluid and the salinity of the water phase of the second diluted drilling fluid comprises:
    titrating the water phase of the drilling fluid and the water phase of the diluted drilling fluid;
    measuring an electrochemical impedance of the water phase of the drilling fluid and the water phase of the diluted drilling fluid;
    measuring an electrical conductivity of the water phase of the drilling fluid and the water phase of the diluted drilling fluid;
    measuring a dielectric constant of the water phase of the drilling fluid and the water phase of the diluted drilling fluid; or
    measuring a thermal conductivity of the water phase of the drilling fluid and the water phase of the diluted drilling fluid.

6. The method of claim 2, wherein measuring the salinity of the water phase of the diluted drilling fluid, the salinity of the water phase of the second diluted drilling fluid, and the salinity of the water phase of the third diluted drilling fluid comprises:
    titrating the water phase of the drilling fluid and the water phase of the diluted drilling fluid;
    measuring an electrochemical impedance of the water phase of the drilling fluid and the water phase of the diluted drilling fluid;
    measuring an electrical conductivity of the water phase of the drilling fluid and the water phase of the diluted drilling fluid;
    measuring a dielectric constant of the water phase of the drilling fluid and the water phase of the diluted drilling fluid; or
    measuring a thermal conductivity of the water phase of the drilling fluid and the water phase of the diluted drilling fluid.

7. The method of claim 1, wherein the one or more drilling parameters comprises a composition of the drilling fluid, a solids removal treatment, a rate of penetration (ROP), a flow rate of the drilling fluid, or any combination thereof.

8. The method of claim 1, wherein:
    the drilling fluid comprises an oil-based drilling fluid or a water-based drilling fluid, and
    the method further comprises determining: (i) an oil/water ratio of the oil-based drilling fluid, or (ii) determining an average specific gravity of solids for the oil-based drilling fluid or water-based drilling fluid, or both.

9. The method of claim 1, further comprising communicating the calculated initial water content to a drill crew.

10. The method of claim 1, wherein the drilling fluid comprises an oil-based drilling fluid.

* * * * *